United States Patent
Temple

(10) Patent No.: US 9,795,287 B2
(45) Date of Patent: Oct. 24, 2017

(54) SYSTEM FOR SIMULTANEOUSLY HEATING MULTIPLE SURGICAL VIEWING INSTRUMENTS

(71) Applicant: John Temple, Chelsea, MI (US)

(72) Inventor: John Temple, Chelsea, MI (US)

( * ) Notice: Subject to any disclaimer, the term of this patent is extended or adjusted under 35 U.S.C. 154(b) by 118 days.

(21) Appl. No.: 14/564,744

(22) Filed: Dec. 9, 2014

(65) Prior Publication Data

US 2015/0157190 A1     Jun. 11, 2015

Related U.S. Application Data

(60) Provisional application No. 61/913,547, filed on Dec. 9, 2013.

(51) Int. Cl.
*F27D 11/00* (2006.01)
*A61B 1/06* (2006.01)
(Continued)

(52) U.S. Cl.
CPC .............. *A61B 1/128* (2013.01); *A61B 1/127* (2013.01); *A61B 50/20* (2016.02); *A61B 50/22* (2016.02);
(Continued)

(58) Field of Classification Search
CPC ........... A61B 1/128; A61B 1/127; A61B 1/12; A61B 1/041; A61B 1/05; A61B 1/126; A61B 1/0638; A61B 1/121; A61B 1/00101; A61B 1/00165; A61B 1/00096; A61B 1/00131; A61B 2017/0023; A61B 19/26; A61B 46/10; A61B 46/23; A61B 50/00; A61B 50/10; A61B 50/13; A61B 50/15; A61B 50/18; A61B 2050/0016–2050/0018; A61B 2050/005; A61B 2050/0051–2050/0062; A61B 2050/0065–2050/0067; A61B 2050/105; A61B 2050/21; A61B 50/20; A61B 50/22;
(Continued)

(56) References Cited

U.S. PATENT DOCUMENTS 3,751,629 A * 8/1973 Eisler .................... A47J 36/022
                                                        219/201
5,351,675 A   10/1994 Brodsky
(Continued)

FOREIGN PATENT DOCUMENTS

WO   WO-2005096916   10/2005

*Primary Examiner* — Quang D Thanh
*Assistant Examiner* — Ket D Dang
(74) *Attorney, Agent, or Firm* — John G. Posa; BELZER PC

(57) ABSTRACT

A system for simultaneously heating multiple elongated surgical viewing instruments comprises a heater with a slot and an insert received by the slot. The insert has multiple elongate cavities, each configured to receive the tip of a viewing instrument. A cover, configured to cover the heater with the insert in the slot thereof, provides a plurality of openings aligned with the cavities of the insert. In the preferred embodiment, the heater is reusable and the insert and cover are disposable. The insert and cover may be integrally joined into a single unit. The system may further include a stand upon which the heater is supported, one or more cavities to receive cleaning swabs to be heated, and/or a pad to heat a cleaning wipe or other article.

5 Claims, 3 Drawing Sheets

(51) Int. Cl.
*A61B 1/12* (2006.01)
*A61B 50/26* (2016.01)
*A61B 50/22* (2016.01)
*A61B 50/20* (2016.01)
*A61B 50/24* (2016.01)
*A61B 50/30* (2016.01)
*A47J 27/00* (2006.01)
*H05B 3/00* (2006.01)
*A61B 17/00* (2006.01)

(52) U.S. Cl.
CPC .............. *A61B 50/24* (2016.02); *A61B 50/26* (2016.02); *A61B 50/30* (2016.02); *A47J 27/004* (2013.01); *A61B 1/126* (2013.01); *A61B 2017/0023* (2013.01); *H05B 3/00* (2013.01)

(58) Field of Classification Search
CPC ......... A61B 50/24; A61B 50/26; A61B 50/30; A47J 27/004; A47J 27/0802; A47J 36/24; H05B 3/00; H05B 3/50; H05B 3/32; H05B 3/80; H05B 3/16; H05B 3/48; H05B 2203/003; B29C 65/34; A61M 3/0245; A61M 5/44; A61F 7/00; A61F 7/007; A61F 7/0097; A61F 7/0241; A61F 7/03; A61F 7/034; A61F 7/08; A61F 7/086; A61F 2007/0098; A61F 2007/0268; A61F 2007/023; A61F 2007/0238; A61F 2007/0269; A61F 2007/0279; A61F 2007/105; A61H 2201/0157; A61H 2201/02; A61H 2201/0207; A61H 2201/0221; A61H 2201/0228; A61H 2201/0242; A61H 2201/0271; A61H 2201/0278
USPC ....... 219/429, 438, 385, 430, 431, 432, 433, 219/434, 436, 530–540, 544, 546; 600/155, 101, 129, 157, 169, 160, 133, 600/175–177, 102, 300, 1; 128/897–898, 128/849–856; 601/15, 16; 607/96–114
See application file for complete search history.

(56) References Cited

U.S. PATENT DOCUMENTS

| | | | |
|---|---|---|---|
| 5,413,092 A | 5/1995 | Williams, III et al. | |
| 5,654,757 A | 8/1997 | Murakami et al. | |
| 5,910,106 A | 6/1999 | Morgan et al. | |
| 6,686,563 B1 * | 2/2004 | Pearlman | A47J 27/004 219/214 |
| 6,707,008 B2 * | 3/2004 | Roehr | A47F 3/001 219/214 |
| 6,936,794 B2 * | 8/2005 | Zhang | A47F 3/001 219/385 |
| 7,311,650 B2 | 12/2007 | Makar et al. | |
| 7,311,660 B2 | 12/2007 | Gomez | |
| 7,537,563 B2 | 5/2009 | Temple | |
| 8,152,717 B2 | 4/2012 | Gomez | |
| 8,258,440 B2 * | 9/2012 | Shei | A21B 3/00 219/483 |
| 8,267,896 B2 | 9/2012 | Hartoumbekis et al. | |
| 8,338,756 B2 * | 12/2012 | Shei | A21B 3/00 219/402 |
| 2002/0022762 A1 | 2/2002 | Beane et al. | |
| 2005/0238530 A1 * | 10/2005 | Frieze | A61L 2/07 422/1 |
| 2009/0247832 A1 * | 10/2009 | Temple | A61B 1/127 600/169 |
| 2010/0140251 A1 * | 6/2010 | Shei | A21B 3/00 219/430 |
| 2010/0140252 A1 * | 6/2010 | Shei | A21B 3/00 219/482 |
| 2011/0014342 A1 * | 1/2011 | Picozza | A47J 36/2433 426/474 |
| 2012/0074121 A1 * | 3/2012 | Gagas | A47J 36/2483 219/385 |
| 2012/0152289 A1 * | 6/2012 | Smith | A61L 2/26 134/109 |
| 2013/0150674 A1 | 6/2013 | Haig et al. | |

* cited by examiner

# SYSTEM FOR SIMULTANEOUSLY HEATING MULTIPLE SURGICAL VIEWING INSTRUMENTS

REFERENCE TO RELATED APPLICATION

This application claims priority from U.S. Provisional Patent Application Ser. Nos. 61/913,547, filed Dec. 9, 2013, the entire content of which is incorporated herein by reference.

FIELD OF THE INVENTION

This invention relates generally to surgical instruments and supplies and, in particular, to a system for heating multiple medical/surgical viewers subject to fogging.

BACKGROUND OF THE INVENTION

In minimally invasive surgical (MIS) procedures, elongated illuminators and viewers, i.e., laparoscopes and endoscopes, are inserted through small incisions in the abdominal wall or elsewhere. The viewer is typically coupled to a video camera that shows the operating field on a monitor.

A common problem is that the lens on the viewer becomes fogged. When the viewer is inserted, the lens is typically at operating room temperature which is often much colder than room temperature. The body cavity is at body temperature and high humidity. As such, water droplets condense on the lens, obscuring the view. When the lens fogs, the surgeon must remove the instrument, clean the lens, and reinsert the instrument at which time fogging often begins again.

To address this problem, the instrument may be immersed in a warm saline bath before surgery and during cleaning. This can be time-consuming and it is difficult to control temperature to consistent, effective working temperature.

An automated approach is described in Published U.S. Patent Application 2002/0022762. A lens warming and cleaning device for use with an optical surgical instrument is disclosed. The device includes a heat-conducting tube sized and shaped to receive the lens portion of the instrument, a heating element thermally coupled to an exterior of the tube, and a cleaning member disposed within the tube. The cleaning member is disposed such that when the lens portion of the instrument is inserted into the tube, the lens portion contacts the cleaning member. The heating element comprises a flexible pad that surrounds at least a portion of the tube including the lens portion. The pad may be wrapped around tube or attached to tube using an adhesive or hook-and-loop fasteners.

In one disclosed embodiment, the heating pad includes a flexible, air-permeable outer bag that encases a chemical mixture that generates an exothermic reaction when activated. The chemical mixture can be, e.g., a mixture of iron powder, water, cellulose, vermiculite, activated carbon, and salt. Exposing the mixture to atmospheric oxygen triggers an exothermic reaction that warms the pad to a temperature of about 60° C. and sustains that temperature for about six hours.

Other types of known exothermic reaction mixtures can be used. For example, the mixture can consist of iron powder, a chloride or sulfate of a metal having a tendency of ionization greater than iron, active carbon, and water. Alternatively, the chemical mixture can be a super-cooled, supersaturated aqueous solution of sodium acetate. The pad can also employ other types of exothermic chemical reactions to generate heat, or it can include a resistance heater powered by, e.g., a battery or an external source of electricity.

The problems with this system are two-fold. First, the addition of a cleaning mechanism is all embodiments constitutes an unnecessary complication, since warming is by far the greatest need. Additionally, although "other types of exothermic chemical reactions" are mentioned in passing, activation methods and apparatus are not disclosed.

Another issue with all commercially available scope warmers is that only a single instrument may be heated at a given time. Many procedures, however, require multiple viewing instruments that may need to be warmed more than once during an operation. Accordingly, the need remains for a less expensive yet effective endoscope/laparoscope warming system, particularly one that accommodates multiple instruments at the same time.

SUMMARY OF THE INVENTION

This invention resides in a system for simultaneously heating multiple elongated surgical viewing instruments. The system comprises a heater with a slot and an insert received by the slot. The insert has multiple elongate cavities, each configured to receive the tip of a viewing instrument. A cover, configured to cover the heater with the insert in the slot thereof, provides a plurality of openings aligned with the cavities of the insert.

In the preferred embodiment, the heater is reusable and the insert and cover are disposable. The insert and cover may be integrally joined into a single unit. The system may further include a stand upon which the heater is supported, one or more cavities to receive cleaning swabs to be heated, and/or a pad to heat a cleaning wipe or other article

DETAILED DESCRIPTION OF THE INVENTION

This invention improves upon existing scope warmer solutions by providing a system that electrically heats multiple instruments simultaneously, but which uses disposable inserts so that the heating apparatus may be used over and over again without discarding the expensive equipment.

Figure 1:
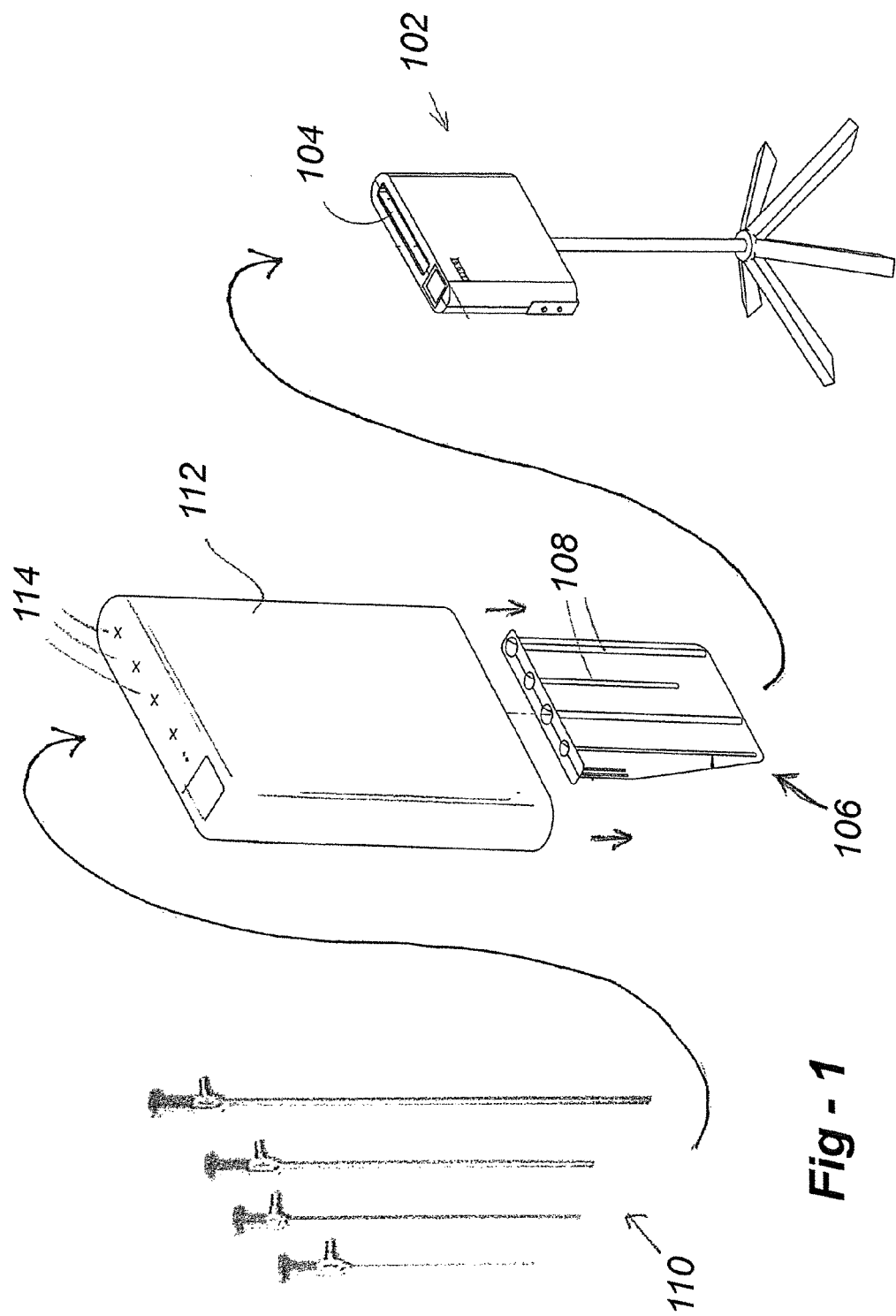
FIG. 1 is an overview of a preferred system according to the invention.

FIG. 1 is an overview of the system. A heating unit 102 with an optional floor stand contains heating elements described below which may be operated by a rechargeable battery or a line cord. Advantageously, the heating unit 102 may be positioned in the sterile field.

Unit 102 includes a slot 104 dimensioned to receive a disposable insert 106 with elongated cavities 108 configured to receive instruments 110. When the insert 106 is inserted into heater 102, the unit is covered with disposable cover 112 that includes slits 114. Instruments 110 are inserted through the slits and into the cavities of insert 106 where they are heated. Following a procedure, the insert 106 and cover 112 are discarded, enabling the heater 102 to be re-used.

Figure 2:
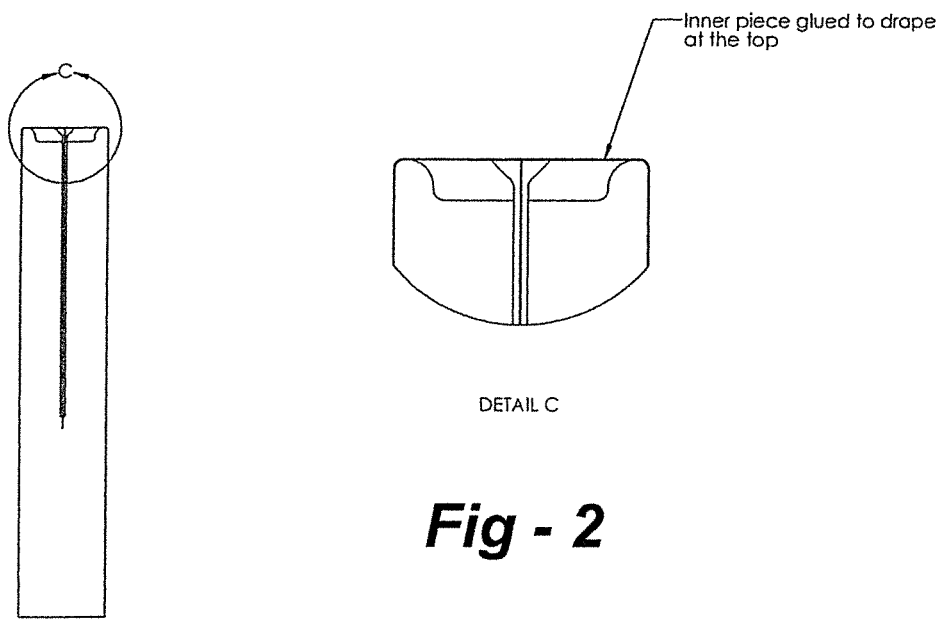
FIG. 2 shows how an insert and cover may be bonded to one another.
Figure 3:
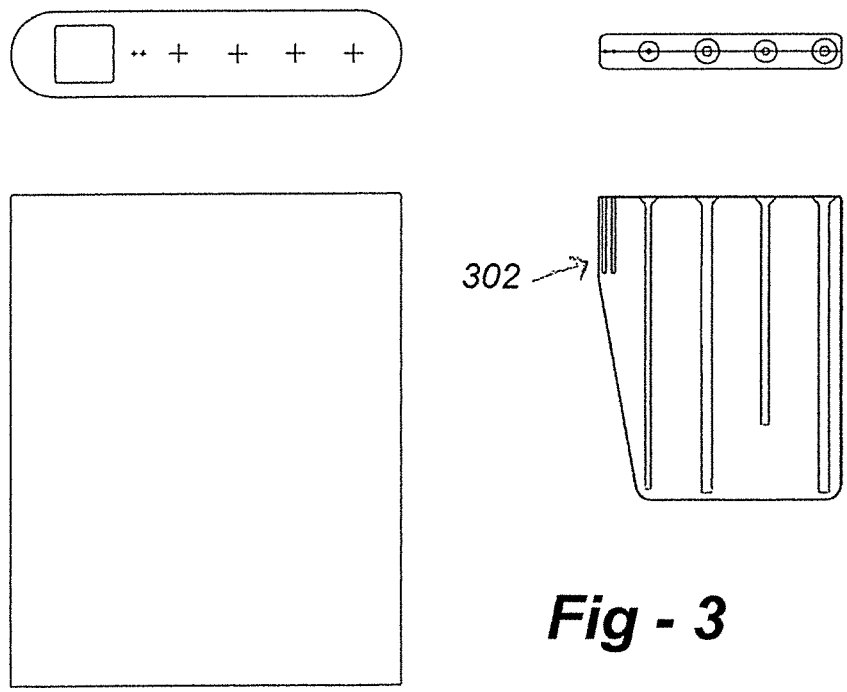
FIG. 3 provides side and top views of the insert and cover.

The insert 106 and cover 112 are provided in a sealed sterilized package prior to use. The insert and cover may be made from any plastic material, though the insert is preferably rigid or semi-rigid whereas the cover may be more flexible. Alternatively if one or both of the insert and cover may be made of a material such as stainless steel in which case they may be autoclaveable and resusable as well. As opposed to separate pieces, the insert and cover may be bonded to one another as shown in FIG. 2 regardless of the material(s) used. In the preferred embodiment, the bottom edge of the cover 112 extends past the bottom of the heater unit 102 to maintain sterility. FIG. 3 gives side and top views of the insert and cover. Optional smaller cavities 302 may be provided to heat cleaning swaps swabs or smaller articles.

Figure 4:
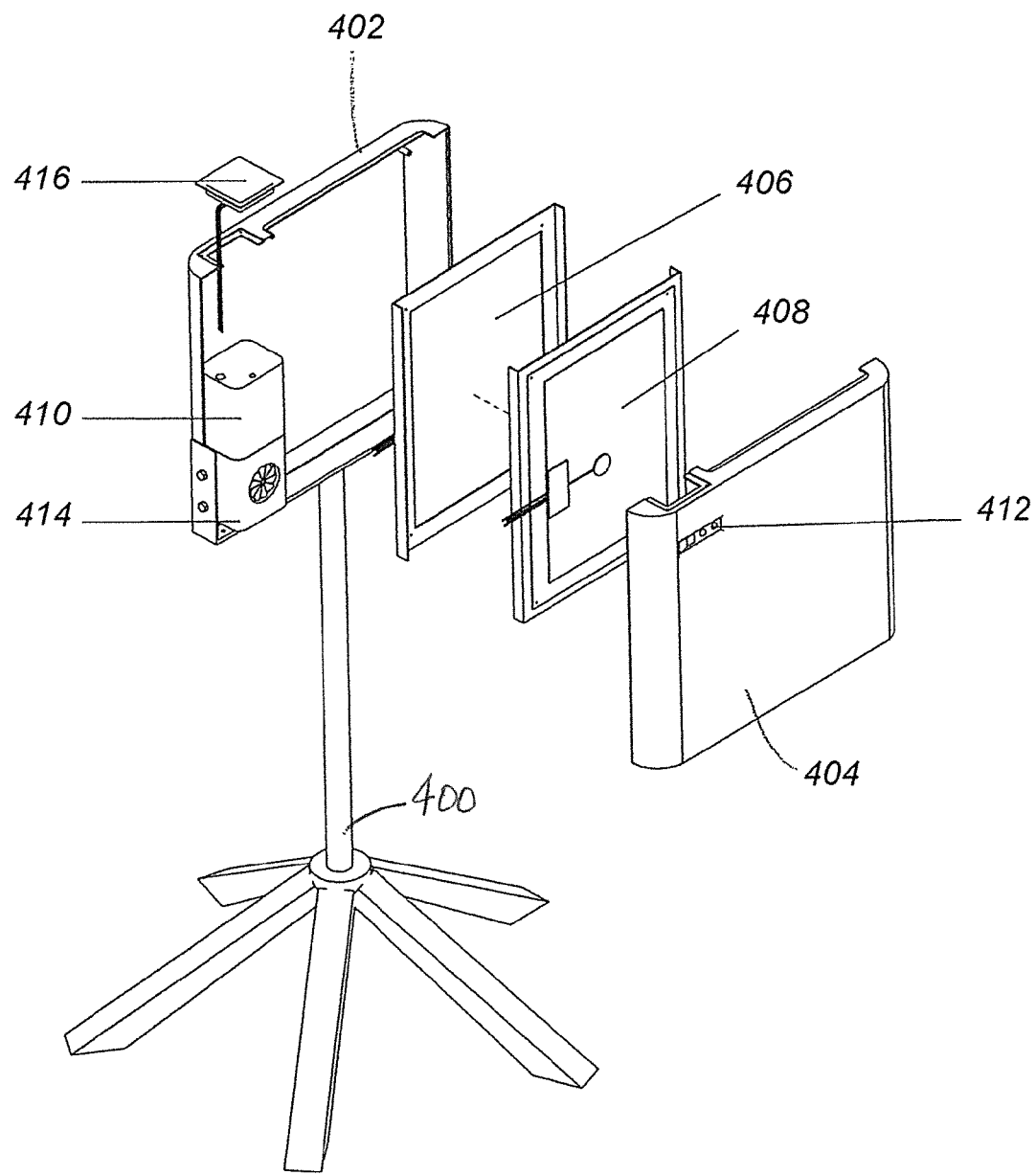
FIG. 4 is an exploded view of a heating unit and floor stand.

FIG. 4 is an exploded view of the heating unit and floor stand 400. Metal plates 406, 408 with attached heaters are disposed with outer covers 402, 404. The heaters are controlled through controller 410 via control panel 412. A fan 414 may be used to improve heat circulation within the enclosure. The system may further include an optional metal dish 416 with attached heater for warming instrument tip cleaning pads or other items.

The invention claimed is:

1. A system for simultaneously heating multiple elongated surgical viewing instruments, comprising:
    a heater with a slot;
    an insert received by the slot, the insert having multiple elongate cavities, each of the elongate cavities being configured to receive a tip of a viewing instrument; and
    a cover configured to cover the heater with the insert in the slot thereof, the cover including a plurality of openings aligned with the cavities of the insert.

2. The system of claim 1, wherein the heater is reusable.

3. The system of claim 1, wherein the insert and the cover are disposable.

4. The system of claim 1, wherein the insert and the cover are joined into a single unit.

5. The system of claim 1, further including a stand upon which the heater is supported.

\* \* \* \* \*